(12) United States Patent
Morishita et al.

(10) Patent No.: US 8,617,057 B2
(45) Date of Patent: Dec. 31, 2013

(54) ENDOSCOPE SYSTEM

(75) Inventors: Koki Morishita, Tokyo (JP); Akira Hasegawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1723 days.

(21) Appl. No.: 11/803,816

(22) Filed: May 16, 2007

(65) Prior Publication Data
US 2007/0270652 A1 Nov. 22, 2007

(30) Foreign Application Priority Data

May 22, 2006 (JP) ................... 2006-141381

(51) Int. Cl.
*A61B 1/12* (2006.01)
*A61B 1/06* (2006.01)

(52) U.S. Cl.
USPC .......................................... 600/156; 600/178

(58) Field of Classification Search
USPC .............. 348/67–70; 600/108, 178, 181, 310, 600/317, 342–343, 476, 478
See application file for complete search history.

(56) References Cited

U.S. PATENT DOCUMENTS

| | | | | |
|---|---|---|---|---|
| 6,026,319 A * | 2/2000 | Hayashi | ........................ | 600/476 |
| 6,293,911 B1 * | 9/2001 | Imaizumi et al. | ............. | 600/160 |
| 6,371,908 B1 * | 4/2002 | Furusawa et al. | ............. | 600/160 |
| 7,062,311 B1 * | 6/2006 | Sendai et al. | ................. | 600/407 |
| 7,768,570 B2 * | 8/2010 | Hasegawa | ..................... | 348/342 |
| 2001/0007920 A1 * | 7/2001 | Hayashi | ........................ | 600/476 |
| 2005/0027166 A1 * | 2/2005 | Matsumoto et al. | .......... | 600/162 |
| 2006/0020169 A1 * | 1/2006 | Sugimoto | ..................... | 600/180 |
| 2006/0058684 A1 * | 3/2006 | Sendai | ........................... | 600/476 |
| 2007/0016077 A1 * | 1/2007 | Nakaoka et al. | .............. | 600/476 |

FOREIGN PATENT DOCUMENTS

| | | |
|---|---|---|
| JP | 6-347707 | 12/1994 |
| JP | 10-201707 | 8/1998 |
| JP | 2006-34415 | 2/2006 |

* cited by examiner

*Primary Examiner* — Philip R Smith
(74) *Attorney, Agent, or Firm* — Scully, Scott, Murphy & Presser, P.C.

(57) ABSTRACT

An endoscope system includes an spouting portion spouting a fluorescent agent and a cleaning liquid, a light source portion emitting excitation light and irradiation light having different spectral characteristics, an optical system transmitting the excitation light or the irradiation light to the object, an image capture portion disposed in a section inserted into the coelom and picking up fluorescence and light having a different spectrum band that are emitted from the object, a spectroscopic portion disposed in an optical pass between the image capture portion and an end of the inserted section and restraining light having the same spectrum band as the excitation light from entering the image capture portion, and a control portion allowing the light source portion to emit excitation light at least once after the spouting portion spouts the fluorescent agent onto the object and before the spouting portion spouts the cleaning liquid.

6 Claims, 8 Drawing Sheets

ENDOSCOPE SYSTEM

BACKGROUND OF THE INVENTION

1. Field of the Invention

The present invention relates to an endoscope system.

This application is based on Japanese Patent Application No. 2006-141381, the content of which is incorporated herein by reference.

2. Description of Related Art

A type of endoscope device has been known which observes affected areas stained with a dye (for example, Japanese Unexamined Patent Application Publication No. Hei 10-201707).

A dye used for staining has an absorption band in the visible region. If an affected area is stained with such a dye, the portion where the dye has been applied can be easily observed with visible light. Thus, the dye facilitates the observation of affected areas with an ordinary endoscope (indigocarmine contrast method).

In order to increase the observation accuracy, a fluorescent agent is applied to the object as an alternative to the dye. Such a fluorescent agent is, however, substantially transparent in normally used concentrations. Hence, the visible light observation with an ordinary endoscope cannot determine whether the fluorescent agent has been sufficiently applied to a desired object, disadvantageously.

BRIEF SUMMARY OF THE INVENTION

According to an aspect of the invention, there is provided an endoscope system including a spouting portion that spouts a fluorescent agent and a cleaning liquid for cleaning the surface of the object onto the object. The fluorescent agent is accumulated in the object or reacts with a specific substance in the object. The endoscope system also has a light source portion that emits excitation light for exciting the fluorescent agent spouted from the spouting portion and irradiation light having different spectral characteristics from the excitation light. An optical system transmits the excitation light or irradiation light from the light source portion to the object. An image capture portion is disposed at a section inserted into the coelom and picks up fluorescence emitted from the object by irradiating the object with the excitation light, and light emitted from the object by irradiating the object with the irradiation light and having a different spectrum band from the fluorescence. A spectroscopic portion is disposed in an optical path between the image capture portion and an end of the section inserted into the coelom and restrains light having the same spectrum band as the excitation light from entering the image capture portion. A control portion allows the light source portion to emit the excitation light at least once after the spouting portion spouts the fluorescent agent onto the object and before the spouting portion spouts the cleaning liquid.

The control portion may control the irradiation light to be emitted before the excitation light is emitted to the object.

The control portion may also control the irradiation light to start the irradiation of the object before the spouting portion spouts the fluorescent agent.

The control portion may control the excitation light and the irradiation light to be exclusively emitted to the object.

The light having a different spectrum band from the fluorescence emitted from the object may be light having a visible band reflected from the object.

DETAILED DESCRIPTION OF THE INVENTION

An endoscope system 1 according to a first embodiment of the invention will now be described with reference to FIGS. 1 to 6.

Figure 1:
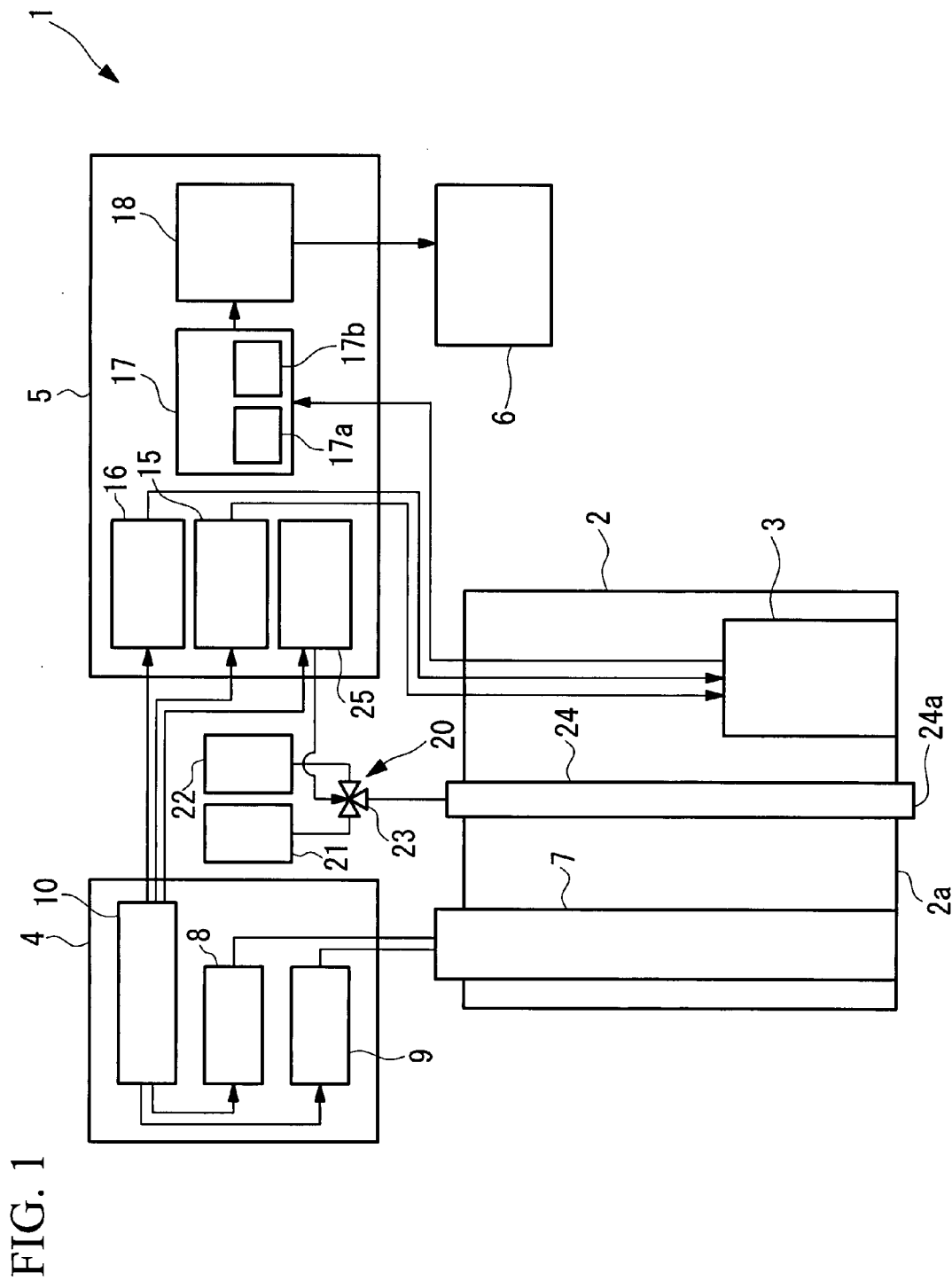
FIG. 1 is a block diagram of the entirety of an endoscope system according to a first embodiment of the invention.

As shown in FIG. 1, the endoscope system 1 includes an insert 2 that is to be inserted into a coelom of a living body, an image capture unit (image capture portion) 3 disposed inside the insert 2, a light source unit 4 emitting a plurality of types of light, liquid delivering unit (spouting portion) 20 that delivers liquid to be spouted from the end 2a of the insert 2, a control unit 5 controlling the image capture unit 3, the light source unit 4 and the liquid delivering unit 20, and a display unit 6 displaying images captured by the image capture unit 3.

The insert 2 is so thin as to be inserted into a coelom of the living body. The insert 2 contains the image capture unit 3 and a light guide (optical system) 7 transmitting light from the light source unit 4 to the end 2a.

The light source unit 4 includes an illumination light source (light source portion) 8 that emits illumination light (irradiation light) illuminating an observation object in the coelom and reflecting from the object, an excitation light source (light source portion) 9 that emits excitation light with which the object in the coelom is irradiated so that a fluorescent substance in the object is excited to emit fluorescence, and a light source control circuit (control portion) 10 controlling the light sources 8 and 9.

The illumination light source 8 is a combination of, for example a xenon lamp and a band-pass filter (those two not shown). The 50% transmission band of the band-pass filter is in the range of 420 to 450 nm; hence, the illumination light source 8 emits illumination light having wavelengths in the range of 420 to 450 nm.

The excitation light source 9 may be a semiconductor laser emitting excitation light having, for example, a peak wavelength of 490±5 nm (or an argon laser emitting excitation light of 488±5 nm). The excitation light having such a wavelength can excite esterase-sensitive fluorescent probes having a fluorescein structure.

Esterase-sensitive fluorescent probes having a fluorescein structure is expressed by the following general formula (1):

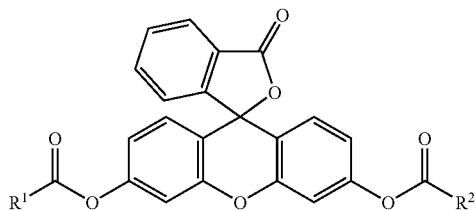

(1)

In this formula, $R^1$ and $R^2$ each represent a substituted or unsubstituted $C_1$-$C_4$ alkyl, a substituted or unsubstituted $C_2$-$C_4$ alkenyl, a substituted or unsubstituted $C_2$-$C_4$ alkynyl, a substituted or unsubstituted aryl, or a substituted or unsubstituted heteroaryl. The compound expressed by general formula (1) provides a tumor cell- or tumor tissue-selective fluorochrome.

In such a fluorochrome, preferably, $R^1$ and $R^2$ are each selected from the group consisting of: $C_1$-$C_4$ alkyl, $C_2$-$C_4$ alkenyl, aryl, and heteroaryl; $C_1$-$C_4$ alkyl and $C_2$-$C_4$ alkenyl; or $C_1$-$C_3$ alkyl and $C_2$-$C_3$ alkenyl. $R^1$ and $R^2$ may each be —CH=CH$_2$.

The aryl group in general formula (1) may be a monocyclic or condensed polycyclic aromatic hydrocarbon. Examples of such aryl include phenyl and naphthyl. The heteroaryl group may be a monocyclic or condensed polycyclic aromatic group whose ring includes at lest one heteroatom, such as nitrogen, oxygen, or sulfur. If the heteroaryl group has two or more heteroatoms, these heteroatoms may be the same or different. Examples of such heteroaryl include furyl, thienyl, pyrrole, pyridyl, imidazolyl, and pyrimidyl.

Exemplary compounds expressed by general formula (1) include a compound whose $R^1$ and $R^2$ are each methyl (fluorescein diacetate: FDA), a compound whose $R^1$ and $R^2$ are each vinyl (fluorescein diacrylate: FDAcr), a compound whose $R^1$ and $R^2$ are each ethyl (FDP), a compound whose $R^1$ and $R^2$ are each n-propyl (FDB), a compound whose $R^1$ and $R^2$ are n-butyl (FDC), a compound whose $R^1$ and $R^2$ are each phenyl (FDBz), and a compound whose $R^1$ and $R^2$ are each 2-furyl (FDFu). However, the esterase-sensitive fluorescent probe is not limited to the above-cited exemplary compounds.

The light source control circuit 10 is configured to alternately turn on and off the illumination light source 8 and the excitation light source 9 at a predetermined timing according a below-described timing chart.

Figure 2:
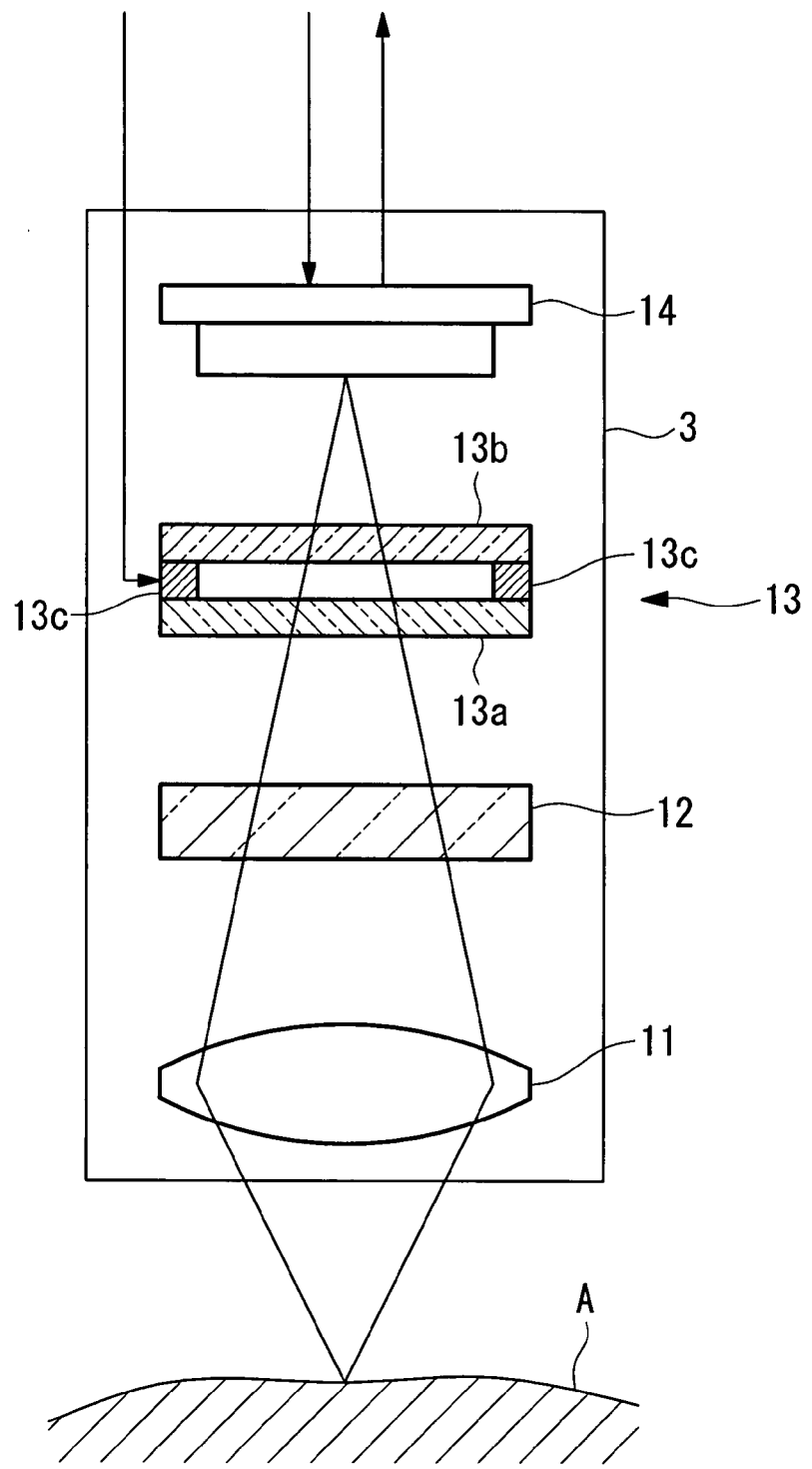
FIG. 2 is a schematic diagram of the interior of an image capture unit of the endoscope system shown in FIG. 1.

Turning now to FIG. 2, the image capture unit 3 includes a image capture optical system 11 collecting light coming from an object A, an excitation light cut filter 12 blocking excitation light coming from the object A, a variable spectroscopic element (variable spectroscopic portion) 13 whose spectral characteristics are varied by the operation of the control unit 5, and an image capture element 14 receiving the light collected by the image capture optical system 11 and converting it into an electrical signal.

The variable spectroscopic element 13 is an etalon optical filter including two opposing flat optical members 13a and 13b and an actuator 13c. The optical members 13a and 13b are disposed parallel to each other with a distance therebetween and whose opposing surfaces are covered with reflection coats. The distance between the optical members 13a and 13b are varied by the actuator 13c. The actuator 13c may be, for example, a piezoelectric element. By varying the distance between the optical members 13a and 13b according to the operation of the actuator 13c, the spectrum band of light transmitted through the variable spectroscopic element 13 can be varied.

Figure 3:
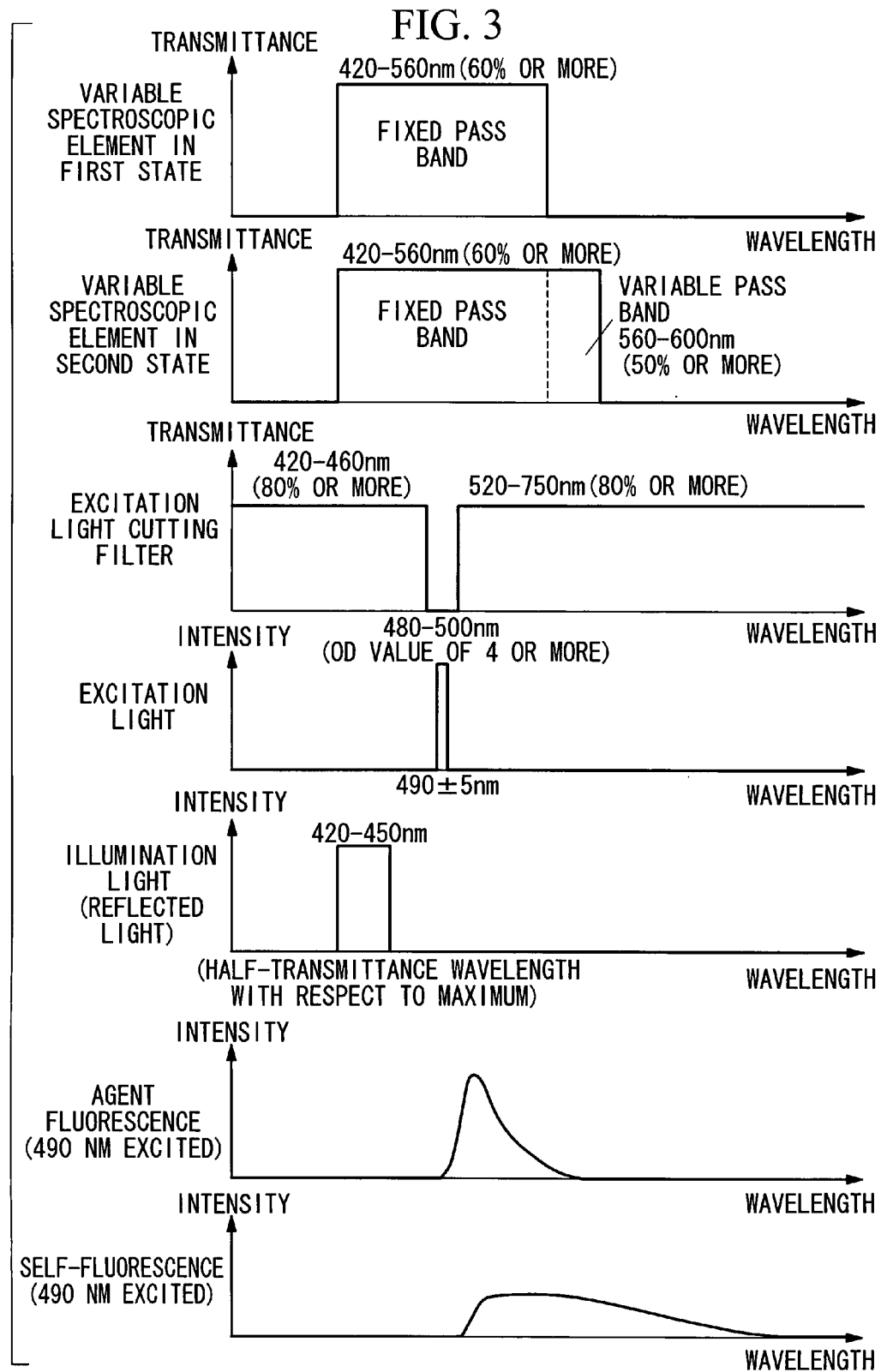
FIG. 3 is a representation showing the characteristics in transmittance with wavelength of optical components of the endoscope system shown in FIG. 1 for irradiation light and fluorescence.

More specifically, as shown in FIG. 3, the variable spectroscopic element 13 exhibits a transmittance-wavelength characteristic having two pass bands: a fixed pass band; and a variable pass band. The fixed pass band is independent of the state of the variable spectroscopic element 13 and in which incident light is always transmitted. The variable pass band varies in transmittance depending on the state of the variable spectroscopic element 13.

In the present embodiment, the variable spectroscopic element 13 has a variable pass band in a red region (for example, in the range of 560 to 600 nm). The variable spectroscopic element 13 switches between two states according to a control signal from the control unit 5.

When the variable spectroscopic element 13 is in a first state, the transmittance in the variable pass band can be sufficiently reduced in comparison with a second state, and the fluorescence of the agent is transmitted. When the variable spectroscopic element 13 is in the second state, the transmittance in the variable pass band is at least 50% increased and the reflection of illumination light is transmitted. As shown in FIG. 3, in the first state, the transmittance in the variable pass band is sufficiently reduced in comparison with the second state so that the variable spectroscopic element 13 can block the self-fluorescence emitted from the living body in the variable pass band, which acts as noises when the fluorescence of the agent is captured, and can transmit the fluorescence of the agent emitted in the fixed pass band. In the second state, the fixed pass band and the variable pass band are set, for example, in the ranges of 420 to 560 nm and 560 to 600 nm respectively, as shown in FIG. 3, so that the variable spectroscopic element 13 can transmit blue, green, and red lights, which are required for R-G-B color observation.

The illumination light may be, for example, in the range of 420 to 450 nm to reflect blood vessel information, as shown in FIG. 3. Red light (580 to 590 nm) may be used as the illumination light, which is less absorbed to the living body and accordingly reflects the shape of its surface more than blue light.

The fixed pass band of the variable spectroscopic element 13 is set for example, in the range of 420 to 560 nm. The transmittance of the variable spectroscopic element 13 is fixed at 60% or more in the fixed pass band.

The fixed pass band is in a spectrum band including the wavelength of the reflection of the illumination light. Consequently, the variable spectroscopic element 13 can transmit the reflected light toward the image capture element 14 in both the first and the second state.

The excitation light cut filter 12 has the following characteristics in transmittance: a transmittance of 80% or more in the spectrum band of 420 to 460 nm; an optical density (OD) of 4 or more (transmittance: $1 \times 10^{-4}$ or less) in the spectrum band of 480 to 500 nm; and a transmittance of 80% or more in the spectrum band of 520 to 750 nm.

The control unit 5 includes an image capture element driving circuit 15 controlling an operation to drive the image capture element 14, a variable spectroscopic element control circuit 16 controlling an operation to drive the variable spectroscopic element 13, a valve control circuit (control portion) 25 described below, a frame memory 17 storing image information obtained by the image capture element 14, and an image processing circuit 18 processing the image information stored in the frame memory 17 and outputting the information to the display unit 6, as shown in FIG. 1.

The image capture element driving circuit 15 and the variable spectroscopic element control circuit 16 are connected to the light source control circuit 10. Consequently, the image capture element driving circuit 15 and the variable spectroscopic element control circuit 16 are configured to control operations to drive the image capture element 14 and the variable spectroscopic element 13 respectively in synchronization with the switching between the illumination light source 8 and the excitation light source 9 by the light source control circuit 10.

Figure 4:
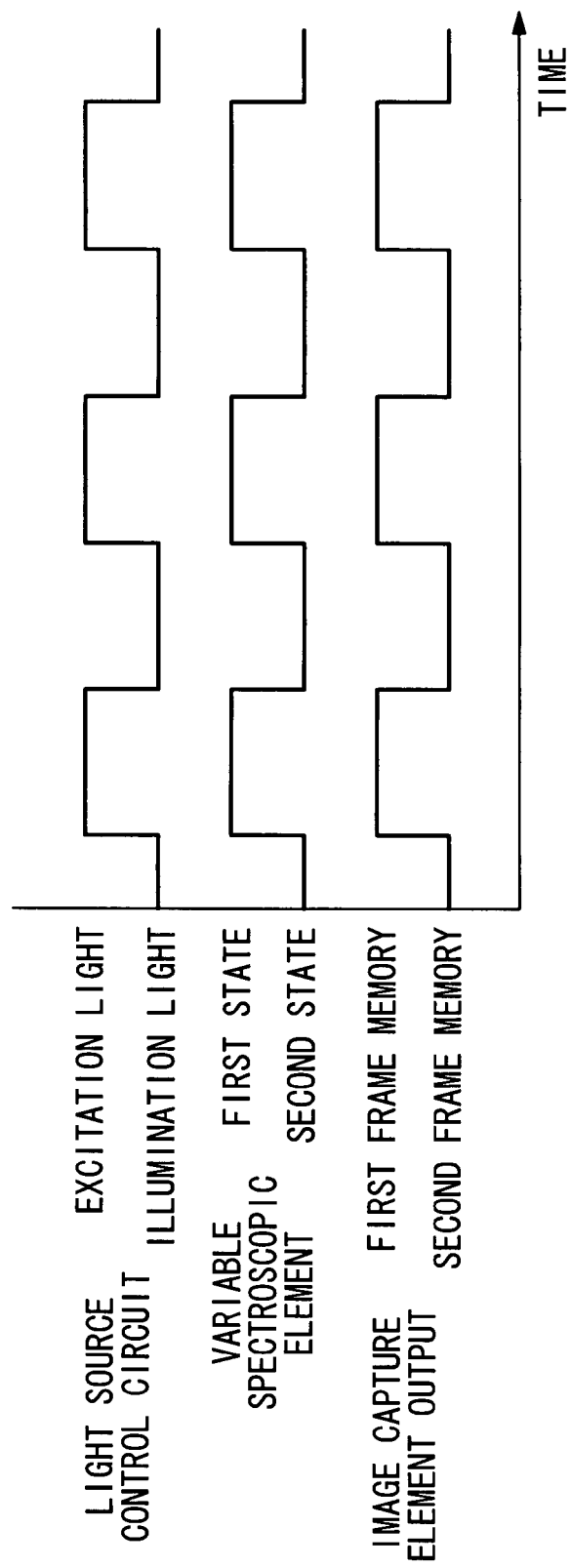
FIG. 4 is a timing chart of the operation of the endoscope system shown in FIG. 1.

More specifically, as shown in the timing chart shown in FIG. 4, when the excitation light source 9 emits excitation light according to an operation of the light source control circuit 10, the variable spectroscopic element control circuit 16 brings the variable spectroscopic element 13 into the first state and the image capture element driving circuit 15 causes the image capture element 14 to output image information to a first frame memory 17*a*. When the illumination light source 8 emits illumination light, the variable spectroscopic element control circuit 16 brings the variable spectroscopic element 13 into the second state and the image capture element driving circuit 15 causes the image capture element 14 to output the image information to a second frame memory 17*b*.

The image processing circuit 18 receives fluorescence image information obtained by, for example, irradiation with excitation light from the first frame memory 17*a* and outputs the information to the red channel of the display unit 6. Also, the image processing circuit 8 receives reflected light image information obtained by irradiation with illumination light from the second frame memory 17*b* and outputs the information to the green channel of the display unit 6.

The liquid delivering unit 20 includes a first reservoir 21 storing cleaning liquid for cleaning the affected area, a second reservoir 22 storing a fluorochrome/probe liquid, a valve 23 selectively delivering or stopping the liquids from the reservoirs 21 and 22, a liquid delivering tube 24 connected to the valve 23 and delivering the liquids to the end 2*a* of the insert 2 along the insert 2, and a valve control circuit 25 disposed in the control unit 5 and controlling the valve 23. The valve 23 may be, for example, a three-way valve. The end 24*a* of the liquid delivering tube 24 is located at the end 2*a* of the insert 2 so that the delivered cleaning liquid or fluorochrome/probe liquid can be spayed onto the object A. The forceps channel of the insert 2 may be uses as the liquid delivering tube 24.

The valve control circuit 25 is connected to the light source control circuit 10. The light source control circuit 10 outputs a valve switching command to the valve control circuit 25 with reference to the timing for switching the light source.

Figure 5:
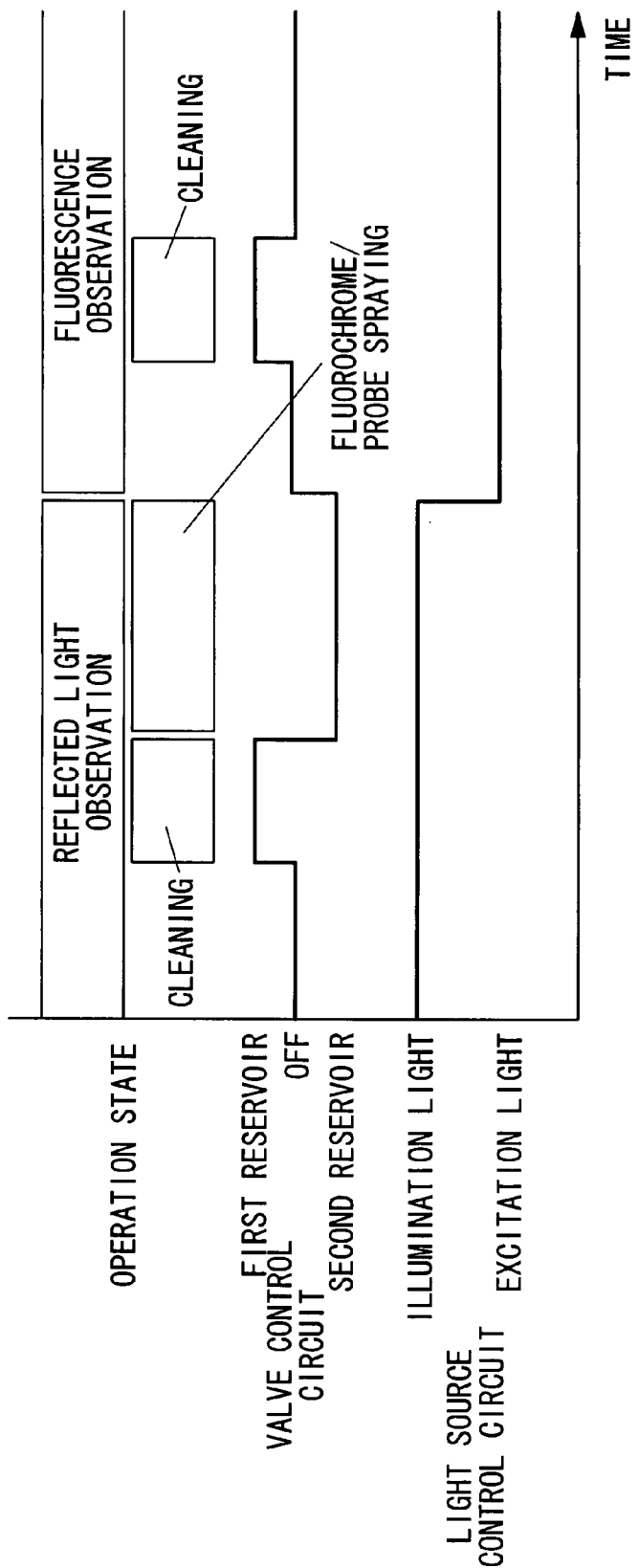
FIG. 5 is a timing chart of a valve control circuit in operation of the endoscope system shown in FIG. 1.

Thus, the valve control circuit 25 causes the cleaning liquid to be spouted from the first reservoir 21 over a predetermined time during reflected light observation, at a predetermined time before switching to the excitation light source 9 according to a switching command from the light source control circuit 10, as shown in FIG. 5. After spouting the cleaning liquid, the valve control circuit 25 controls the valve 23 to spray the fluorochrome/probe liquid from the second reservoir 22.

After spraying the fluorochrome/probe liquid, the valve control circuit 25 switches the valve 23 off. Then, the valve control circuit 25 controls the valve 23 to spout the cleaning liquid from the first reservoir 21 at a predetermined time after switching to the excitation light source 9 according to a switching command from the light source control circuit 10.

The endoscope system 1 according to the present embodiment configured as above operates as described below.

Figure 6:
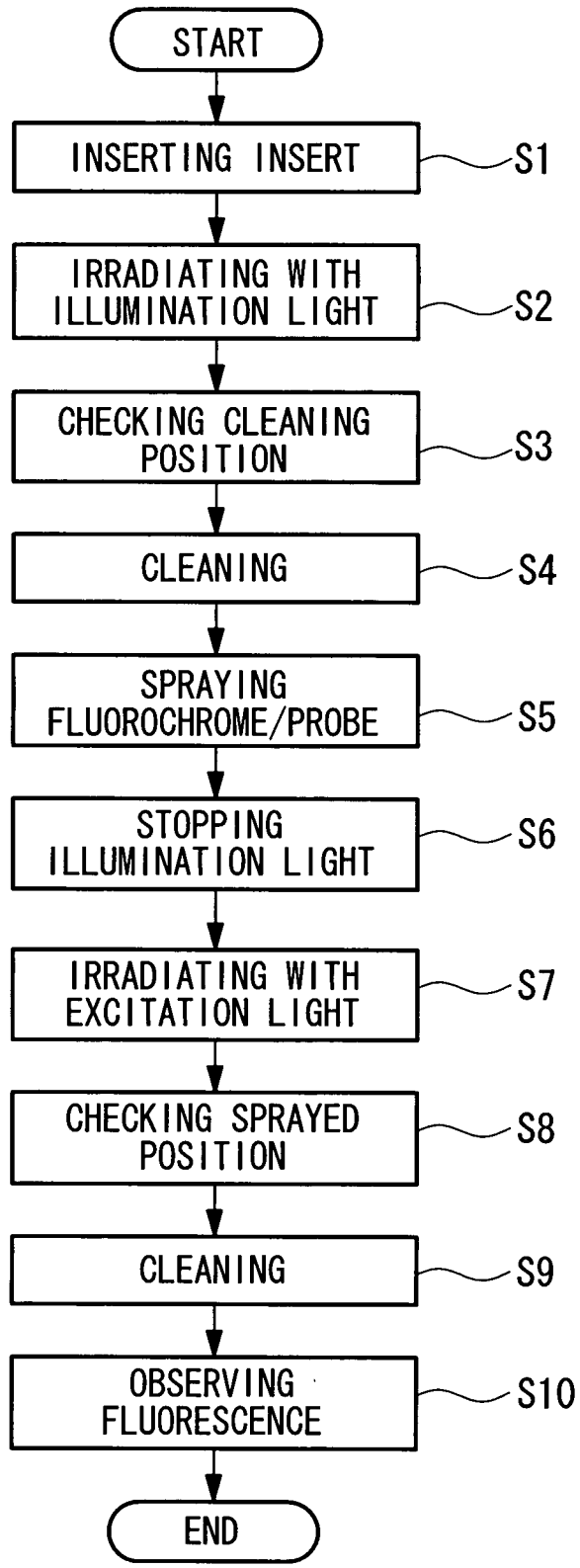
FIG. 6 is a flow chart of the observation using the endoscope system shown in FIG. 1.

For observing an object A in a coelom of the living body with the endoscope system 1 of the present embodiment, first, the insert 2 is inserted into the coelom (Step S1) and the end 2*a* of the insert 2 is opposed to the object A in the coelom, as shown in FIG. 6. In this state, the light source unit 4 and the control unit 5 are brought into operation so that the illumination light source 8 and the excitation light source 9 are alternately emit illumination light and excitation light respectively, according to the operation of the light source control circuit 10.

In reflected light observation (steps S2 to S6) performed with irradiation with illumination light, cleaning is performed (Step S4) while the cleaning point is checked using the reflection of the illumination light (Step S3). After cleaning, the fluorochrome/fluorescent probe is sprayed (Step S5). After spraying the fluorochrome/fluorescent probe, the system is switched to fluorescence observation (Steps S7 to S10), and the state of the region where the fluorochrome/fluorescent probe has been sprayed is checked (Step S8) using fluorescence before cleaning the sprayed region (Step S9). After cleaning the sprayed region, the fluorescence of the sprayed region is observed (Step S10).

The excitation light and the illumination light from the light source unit 4 are transmitted to the end 2*a* of the insert 2 through the light guide 7 and emitted onto the object A from the end 2*a* of the insert 2.

When the object A is irradiated with the excitation light, the fluorescent agent permeated in the object A is excited to emit fluorescence. The fluorescence emitted from the object A is collected by the image capture optical system 11 of the image capture unit 3 and enters the variable spectroscopic element 13 through the excitation light cut filter 12.

The variable spectroscopic element 13 is switched to the first state in synchronization with the operation of the excitation light source 9 according to the operation of the variable spectroscopic element control circuit 16. Thus, the variable spectroscopic element 13 transmits the incident fluorescence because the transmittance of the variable spectroscopic element 13 is sufficiently increased in a region including the spectrum band of the fluorescence. In this instance, part of the excitation light with which the object A is irradiated is reflected from the object A and enters the image capture unit 3 with the fluorescence. However, the image capture unit 3 has the excitation light cut filter 12 and the excitation light is removed not to enter the image capture element 14.

The fluorescence transmitted through the variable spectroscopic element 13 enters the image capture element 14 and the image information of the fluorescence is obtained. The obtained fluorescence image information is stored in the first frame memory 17*a*, and is output to the red channel of the display unit 6 by the image processing circuit 18. Thus, the display unit 6 displays the information.

When the object A is irradiated with the illumination light, the illumination light is reflected at the surface of the object A. The illumination light reflected from the object A is collected by the image capture optical system 11 and enters the variable spectroscopic element 13 through the excitation light cut filter 12. Since the reflected light of the illumination light has a spectrum band in the fixed pass band of the variable spectroscopic element 13, the variable spectroscopic element 13 transmits the entirety of the reflected light entering the variable spectroscopic element 13.

Then, the reflected light transmitted through the variable spectroscopic element 13 enters the image capture element 14 and the image information of the reflected light is obtained. The obtained image information of the reflected light is stored in the second frame memory 17*b*, and is output to the green channel of the display unit 6 by the image processing circuit 18. Thus, the display unit 6 displays the information.

In this instance, the variable spectroscopic element 13 is switched to the second state in synchronization with the operation of the illumination light source 8 according to the operation of the variable spectroscopic element control circuit 16. Since, in this instance, the transmittance of the variable spectroscopic element 13 is reduced in the fluorescence spectrum band, the fluorescence is blocked even if the fluorescence enters, and consequently the image capture element 14 picks up only the reflected light.

In the endoscope system 1 of the present embodiment, the reflected light is observed before observing the fluorescence according to the operation of the light source control circuit 10 and the valve control circuit 25. For reflected light observation, the light source control circuit 10 operates the illumination light source 8 to emit illumination light to the object.

For switching from the reflected light observation to the fluorescence observation, the valve control circuit 25 switches the valve 23 to the first reservoir 21 side before emitting the excitation light, with the illumination light source 8 emitting the illumination light. Thus, the cleaning liquid stored in the first reservoir 21 is spouted from the end 24a of the liquid delivering tube 24 to the object A, thereby cleaning the surface of the object A.

In the present embodiment, the object A is cleaned with the illumination light source 8 emitting the illumination light. Thus, the affected area is easily observed and the cleaning can be performed while the position to which the fluorochrome should be sprayed is checked.

The fluorochrome/fluorescent probe is also sprayed with the illumination light source 8 emitting the illumination light. Thus, a small amount of fluorochrome/fluorescent probe can be accurately sprayed on a desired position while the position of the object A that has been cleaned is checked so that the spray does not deviate from the that position.

Then, when the light source control circuit 10 operates the excitation light source 9 to irradiate the object A with the excitation light, the valve control circuit 25 receives a signal from the light source control circuit 10 to switch the valve 23 off.

In this instance, in the present embodiment, the excitation light source 9 emits the excitation light after spraying the fluorochrome/fluorescent probe and before cleaning. Thus, the state of the sprayed position can be checked because of the fluorescence even if the fluorochrome is transparent.

Thus, the observation with the endoscope system 1 of the present embodiment allows the esterase-sensitive fluorescent probe to be accurately sprayed to a position suspected to be cancer, and helps determine whether the suspected position is cancer or not. In this instance, the esterase-sensitive fluorescent probe is not distributed throughout the body by blood flow, and a small amount of esterase-sensitive fluorescent probe can immediately identify a tumor cell site and thus detect it at the moment when it is observed. Hence, the amount of expensive fluorescent agent can be minimized to reduce the cost of observation, compared with administrating oral, intravenous doses, etc. (a large amount of medication).

The endoscope system 1 of the present embodiment can provide a composite image of a fluorescent image and a reflected light image to the user.

Since the endoscope system 1 uses the variable spectroscopic element 13 that can vary the light transmittance simply by varying the distance between the flat optical members 13a and 13b, a significantly small variable spectroscopic element 13 and image capture element 14 can be disposed at the end 2a of the insert 2. Accordingly, it is not necessary to extract the fluorescence and the reflected light from the object A to the outside through a fiber bundle.

The apparatus of the present embodiment can capture not only feeble fluorescent images whose quality is liable to be degraded due to noises but also other images. Accordingly, affected areas can be efficiently checked.

The light source unit 4 in the present embodiment switches the states of the variable spectroscopic element 13 in synchronization with the switching between the light sources 8 and 9. This allows a single image capture element 14 to capture a plurality of types of light having different spectrum bands. Consequently, the system does not need to have a plurality of capture optical systems corresponding to the fluorescence and the reflected light; hence the diameter of the insert 2 can be reduced.

Since light capable of passing through tissues of the living body can be present even in coeloms of the living body, it is important to reduce noises when particularly feeble light, such as fluorescence, is observed. In the present embodiment, the image capture unit 3 has the variable spectroscopic element 13 to block light having wavelengths other than those of the object even if the spectrum band to be observed is changed. Consequently, high-quality images can be obtained with noises reduced.

Furthermore, the illumination light source 8 in the present embodiment emits illumination light having a spectrum band of 420 to 450 nm. This spectrum band includes the absorption band of hemoglobin. By picking up the image of the reflection of the illumination light, the information of the structure of a blood vessel relatively close to the surface of the living body can be obtained.

In general, the longer wavelength light has, the less the light is scattered in the living body, and accordingly even fluorescence generated deep in the living body can be easily observed. However, light having a wavelength of 1 μm or more is absorbed by water to attenuate, and thus becomes difficult to observe. By use of a fluorochrome emitting infrared fluorescence as in the endoscope system 1 of the present embodiment, the information of the living body, particularly information of a lesion, such as cancer, produced around a mucosa can be efficiently obtained.

In the image capture unit 3 of the endoscope system 1, the image capture optical system 11, the excitation light cut filter 12, and the variable spectroscopic element 13 are arranged in that order from the end 2a of the insert 2. However, the order of the arrangement is not limited to this and any order can be selected.

The endoscope system 1 of the present embodiment uses an esterase-sensitive fluorescent probe having a fluorescein structure as the fluorochrome/probe. However, instead of such an esterase-sensitive fluorescent probe, a cyanine compound, such as a fluorescent probe having a tricarbocyanine structure, may be used singly or in combination with a compound expressed by the above-described general formula (1) as the fluorescent probe. The present invention provides such diagnostic products and contrast media.

Figure 7:
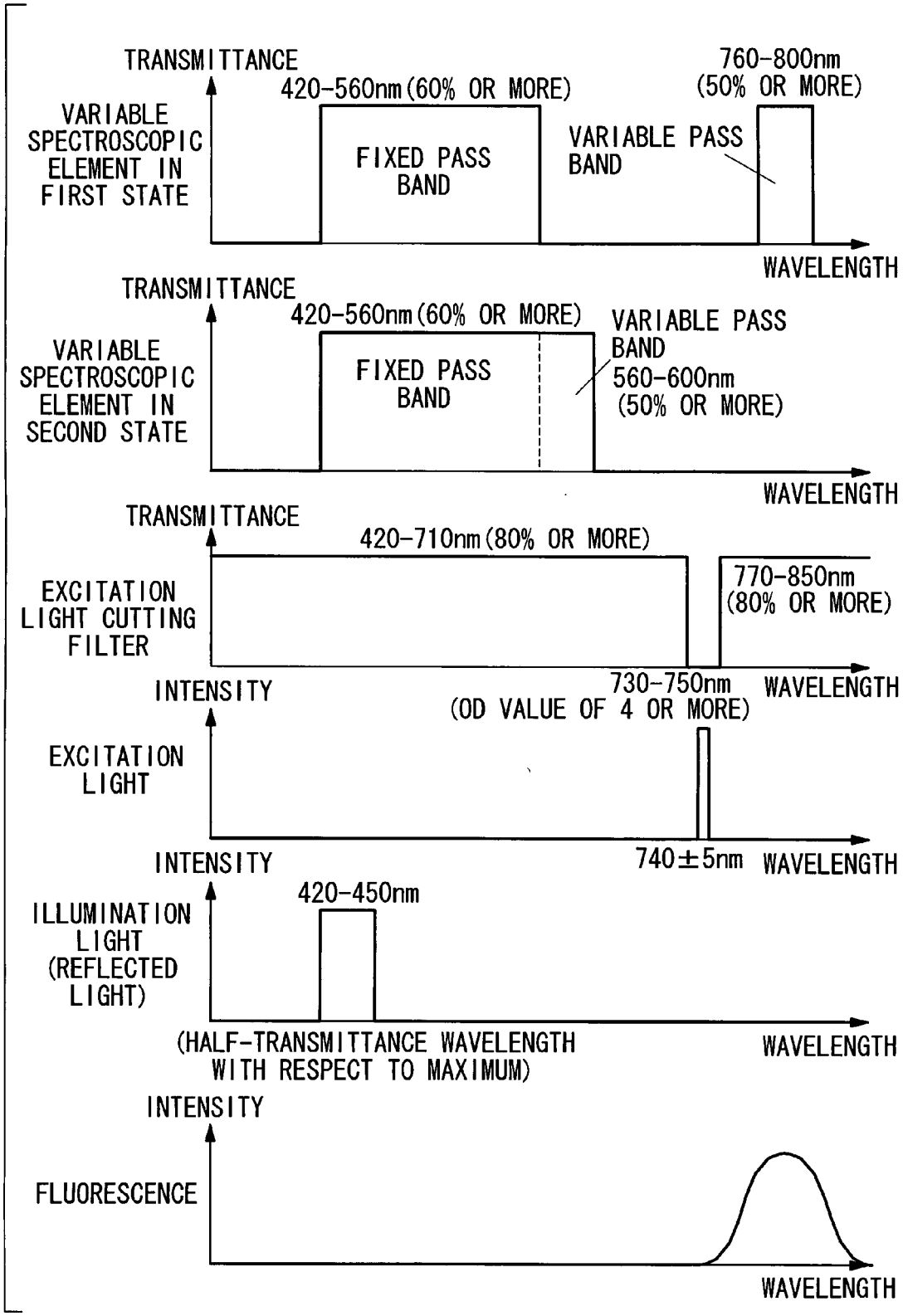
FIG. 7 is a representation of the characteristics in transmittance with wavelength of optical components of the endoscope system shown in FIG. 1 using a fluorescentmolecule/probe having carbocyanine structure for irradiation light and fluorescence.

If the endoscope system is used for observation using such a diagnostic product or contrast medium, the variable spectroscopic element 13 has a variable pass band in a spectrum band (for example, 760 to 800 nm) including the wavelength of fluorescence (of the agent) emitted by exciting the fluorochrome/probe with excitation light, as shown in FIG. 7. The variable spectroscopic element 13 in the first state increases the transmittance in the variable pass band to 50% or more to transmit the fluorescence of the agent. In the second state, the spectrum band of the variable pass band is shifted to, for example, 560 to 600 nm so that the variable spectroscopic element 13 can block the fluorescence of the agent.

The excitation light cut filter 12 has a transmittance of 80% or more in the spectrum band of 420 to 710 nm, an optical density (OD) of 4 or more (transmittance: $1 \times 10^{-4}$ or less) in the spectrum band of 730 to 750 nm, and a transmittance of 80% or more in the spectrum band of 770 to 850 nm.

The excitation light source 9 may be a semiconductor laser emitting excitation light having, for example, a peak wavelength of 740±5 nm. The excitation light having such a wavelength can excite fluorescentmolecule/probe having carbocyanine structures, such a fluorescent probe having a tricarbocyanine structure.

By use of such an excitation light source 9, the same effect as in use of the esterase-sensitive fluorescent probe having a fluorescein structure can be produced.

When the image of a coelom of the living body is picked up, the brightness of the fluorescent image of the agent is generally extremely lower than that of the reflected light image. As a result, it may be required that the amount (light exposure) of light entering the image capture element 14 be appropriately adjusted each time of switching between the reflected light image observation and the agent fluorescence image observation.

Accordingly, in order for the fluorescent endoscope system described above to operate according to the brightness of the image measured by the image capture element 14 and to adjust the brightness of the image close to a predetermined desired value, it is preferable that the control unit 5 adjust the light exposure of the image capture unit 3 (image capture element 14) for capture, in addition to switching the irradiation light (excitation light) of the light source unit 4 and the spectral characteristics of the variable spectroscopic element 13. For controlling the light exposure, more specifically, it is preferable to perform at least one adjustment of the illumination light (excitation light) from the light source portion 4 (emission intensity or duration of emission), the exposure of the image capture unit 5 (shutter speed or diaphragm), and the amplification factor of the image capture unit 5.

Such adjustment is more important particularly when images having extremely different brightnesses and high-brightness regions (bright regions) form a single image, such as a combination of a reflected light image whose entirety is relatively bright and a fluorescent image of the agent whose fluorescent region is limited to the region where the agent is applied (administered).

The brightness used for adjusting the brightness may be measured in an averaging metering mode in which the brightness is defined as the average of the entirety or part of the image or in a peak metering mode in which the brightness is defined as the highest value in the entirety or part of the image.

Figure 8:
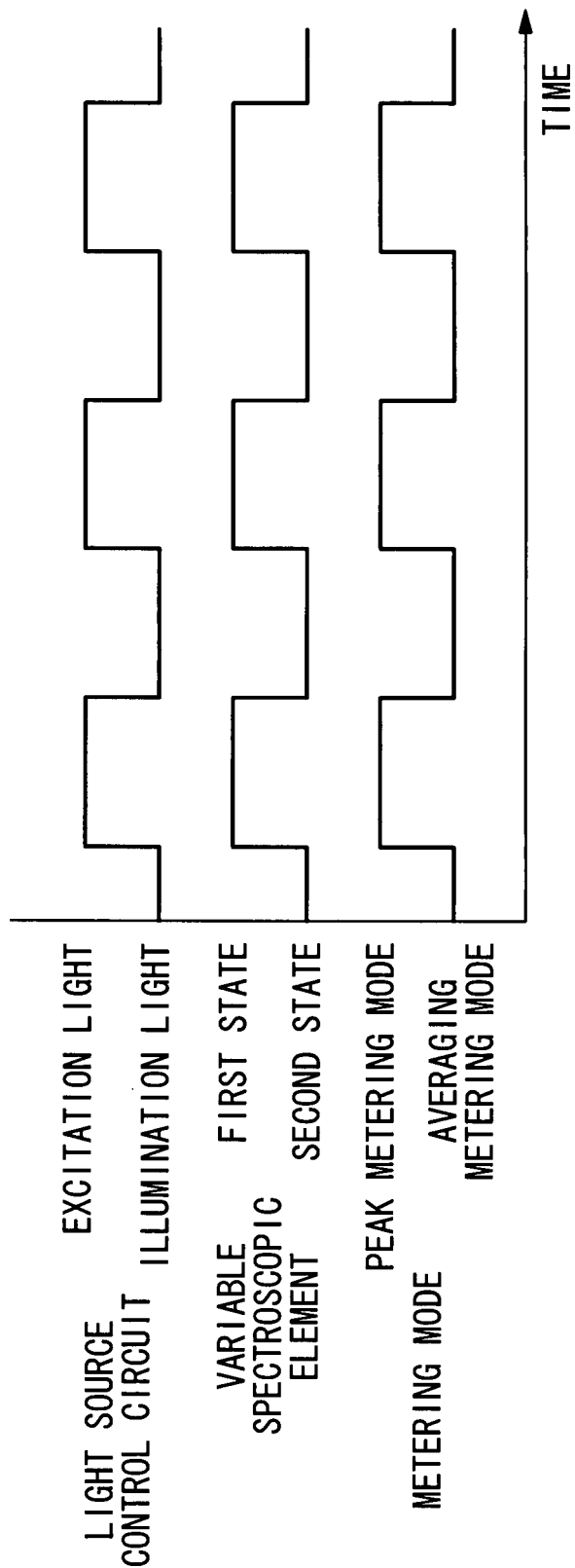
FIG. 8 is an exemplary timing chart of the photometric mode switching for capturing an image.

It is further preferable that the mode for measuring the brightness of an image be controlled at a predetermined timing according to the timing chart shown in FIG. 8 in association with the light source control circuit and the variable spectroscopic element control circuit so that the averaging metering mode is set for capturing a reflected light image and the peak metering mode is set for capturing the fluorescent image of the agent.

When a reflected light image is captured, the object is often reflected over the entire image to form a relatively bright region over the entire image. Thus, the averaging metering mode is effective. If peak metering is performed on such a reflected light image, the brightness of an extremely bright region, such as reflection of the mucus of the living body, is adjusted to be close to a desired value and consequently the object is darkened.

When a fluorescent image of the agent is captured, the occurrence of fluorescence is limited to the region where the fluorescent agent is applied (administered). Thus, a large part of the image is often darkened without emitting fluorescence and a small part of the image emits fluorescence of the agent. Thus the peak metering mode is effective.

If averaging metering is performed on such a fluorescent image, the brightness, including that of the dark region occupying a large part of the image, is adjusted so as to be close to a desired value. Consequently, noises of the region emitting no fluorescence are emphasized and the image is difficult to observe.

In the present embodiment, a fluorochrome/fluorescent probe having a rhodamine structure or the like may also be used under conditions in which the spectral characteristics of the excitation light source 9 and spectroscopic portion are optimized.

Examples of such a fluorochrome include fluorescein compounds such as FITC, rhodamine compounds such as Rhodamine B, cyanine compounds such as indocyanine green and CyDye (produced by Amersham), Bodipy compounds such as Bodipy-FL, porphyrin compounds or porphyrin compound precursors, and Alexa Fluor Dye (produced by MolecularProbes). Instead of fluorochromes, an antibody or peptide labeled with such a fluorochrome, such as a labeled antibody of Her 2 receptor, which is often found in breast cancer, and somatostatin (ligand of somatostatin receptor) labeled with Cy 5.5.

Examples of such a fluorescent probe include esterase-sensitive fluorescent probes such as FDA and CFDA (carbosyfluorescein diacetate), NITRIC OXIDE-sensitive fluorescent probes such as DAF and DAA, and highly reactive oxygen species-sensitive fluorescent probes such as HPF, APF, and H2DCFDA.

Fluorescent probes do not emit fluorescence unless they react with a specific substance in the living body, and the state in which a fluorescent probe has been sprayed may not be able to be sufficiently checked before cleaning. Accordingly, a fluorescent probe mixed with a fluorochrome capable of being reliably removed by cleaning (water-soluble fluorochrome) may be sprayed.

While the present embodiment uses an etalon (Fabry-Perot variable spectroscopic element) as the spectroscopic portion, the spectroscopic portion is not limited to an etalon and a variable spectroscopic filter may be used, or the spectroscopic portion may have fixed spectral characteristics.

The fluorescent endoscope system 1 of the invention is not limited to a scope type that has an image capture portion 14 at the end of the insert 2 inserted to a coelom of the living body. For example, the fluorescent endoscope system of the invention may be of a capsule type whose enclosure contains the light source portion, the image capture portion, and the variable spectroscopic portion so that the entirety of the enclosure is inserted into a coelom of the living body.

What is claimed is:

1. An endoscope system capturing an image of an object in a coelom, the endoscope system comprising:
    a spouting portion that spouts a fluorescent agent and a cleaning liquid for cleaning the surface of the object onto the object, the fluorescent agent being accumulated in the object or reacting with a specific substance in the object;
    a light source portion that emits excitation light for exciting the fluorescent agent spouted from the spouting portion and irradiation light having different spectral characteristics from the excitation light;

an optical system that transmits the excitation light or irradiation light from the light source portion to the object;

an image capture portion that is disposed at a section inserted into the coelom and that picks up fluorescence emitted from the object by irradiating the object with the excitation light, and light emitted from the object by irradiating the object with the irradiation light and having a different spectrum band from the fluorescence;

a spectroscopic portion that is disposed in an optical path between the image capture portion and an end of the section inserted into the coelom and that restrains light having the same spectrum band as the excitation light from entering the image capture portion; and a control portion that controls the spouting portion and the light source portion, wherein the control portion controls the light source portion to emit the excitation light after the spouting portion spouts the fluorescent agent onto the object, and carries out control to spout the cleaning liquid at a predetermined time after the excitation light emission is started.

2. The endoscope system according to claim 1, wherein the control portion controls the irradiation light to be emitted before the excitation light is emitted to the object.

3. The endoscope system according to claim 2, wherein the control portion controls the irradiation light to start the irradiation of the object before the spouting portion spouts the fluorescent agent.

4. The endoscope system according to claim 1, wherein the control portion controls the excitation light and the irradiation light to be exclusively emitted to the object.

5. The endoscope system according to claim 1, wherein the light having a different spectrum band from the fluorescence emitted from the object is light having a visible band reflected from the object.

6. An endoscope system capturing an image of an object in a coelom, the endoscope system comprising:

spouting means for spouting a fluorescent agent and a cleaning liquid for cleaning the surface of the object onto the object, the fluorescent agent being accumulated in the object or reacting with a specific substance in the object;

irradiation light emitting means for emitting excitation light for exciting the fluorescent agent spouted from the spouting means and irradiation light having different spectral characteristics from the excitation light;

optically transmitting means for transmitting the excitation light or irradiation light from the irradiation light emitting means to the object;

image capture means disposed at a section inserted into the coelom for picking up fluorescence emitted from the object by irradiating the object with the excitation light and light emitted from the object by irradiating the object with the irradiation light, the light having a different spectrum band from the fluorescence;

spectroscopic means disposed in an optical path between the image capture means and an end of the section inserted into the coelom, the spectroscopic means restraining light having the same spectrum band as the excitation light from entering the image capture means; and control means for controlling the spouting means and the irradiation light emitting means, wherein the control means carries out control of the irradiation light emitting means to emit the excitation light after the spouting means spouts the fluorescent agent onto the object, and carries out control to spout the cleaning liquid at a predetermined time after the excitation light emission is started.

* * * * *